United States Patent [19]

Wells

[11] 4,405,784

[45] Sep. 20, 1983

[54] METHOD OF MAKING TRIETHYLENEDIAMINE

[75] Inventor: James E. Wells, Ardmore, Pa.

[73] Assignee: Air Products and Chemicals, Inc., Allentown, Pa.

[21] Appl. No.: 278,814

[22] Filed: Jun. 29, 1981

[51] Int. Cl.³ .......................................... C07D 295/2
[52] U.S. Cl. ................................. 544/352; 544/162
[58] Field of Search ...................................... 544/352

[56] References Cited

U.S. PATENT DOCUMENTS

| | | | |
|---|---|---|---|
| 2,467,205 | 4/1949 | Gresham | 544/352 |
| 2,937,176 | 4/1960 | Herrick | 544/352 |
| 2,985,658 | 4/1961 | Krause | 544/352 |
| 3,166,558 | 1/1965 | Masciele | 544/352 |
| 3,172,891 | 3/1965 | Brader | 544/352 |
| 3,297,701 | 1/1967 | Brader | 544/352 |
| 3,342,820 | 8/1967 | Brader | 544/352 |
| 4,036,681 | 7/1977 | Holten | 162/65 |
| 4,049,657 | 9/1977 | Brennan | 544/352 |
| 4,092,316 | 5/1978 | Nieh | 544/351 |
| 4,095,022 | 6/1978 | Brennan | 544/87 |
| 4,103,087 | 7/1978 | Brennan | 544/78 |
| 4,117,227 | 9/1978 | Brennan | 544/170 |

FOREIGN PATENT DOCUMENTS 1494886 12/1977 United Kingdom .
525681 1/1977 U.S.S.R. .

OTHER PUBLICATIONS

Chem. Abs. 86:43742m, Abstract of Guseva et al., Russian Pat. No. 525,681, (1977).
Richard A. Nyquist and Ronald O. Kagel, Infrared Spectra of Inorganic Compounds, 1971, p. 163.

*Primary Examiner*—Robert W. Ramsuer
*Attorney, Agent, or Firm*—Richard A. Dannells, Jr.; E. Eugene Innis; James C. Simmons

[57] ABSTRACT

Strontium diorthophosphate is employed as catalyst for acid catalyzed organic condensation reactions. High conversion and exceptionally high selectivity are obtained by use of strontium diorthophosphate in cyclization reactions such as in the conversion of hydroxyethylpiperazine to triethylenediamine.

9 Claims, No Drawings

METHOD OF MAKING TRIETHYLENEDIAMINE

TECHNICAL FIELD OF THE INVENTION

The present invention relates to organic condensation reactions effected in the presence of solid acidic catalyst and is more particularly concerned with the production of bicylco N-heterocyclic compounds in enhanced yields.

BACKGROUND OF PRIOR ART

Organic synthesis by condensation reactions resulting in the loss of a molecule of water or of ammonia are well known in the art. Certain of such reactions are generally effected in the presence of acidic catalysts. An important area in which such acid catalysis has been employed is in cyclization reactions as in the synthesis of triethylene diamine and its C-substituted homologues. The catalysts more generally used or proposed for use in such cyclization reactions are solid products of the Lewis acid type.

Triethylenediamine, also called diazabicyclo-[2.2.2.]-octane, has been widely employed commercially as a catalyst in organic isocyanate reactions with compounds containing labile hydrogen, as in the production of urethane polymers. Triethylenediamine (sometimes hereinafter referred to as TEDA) was initially prepared in significant quantities by methods such as that described in U.S. Pat. No. 2,937,176, by passing aliphatic amines in vapor phase over acidic cracking catalyst, such as silica-alumina dried gel or acid-activated clays. Numerous other feed stocks as well as other catalysts are disclosed in subsequent patents for preparation of TEDA as well as C-alkyl derivatives thereof.

Typical among these are U.S. Pat. Nos. 2,985,658 and 3,166,558 employing preferably silica-alumina type catalyst, but listing also other useful solid acid catalysts that can be employed such as alumina in which phosphate or fluoride ion is incorporated (U.S. Pat. No. 2,985,658).

Among other catalysts proposed in the patent art for preparation of triethylene diamine and/or C-alkyl homologues thereof, are certain phosphate compounds, particularly aluminum phosphate.

The use of aluminum phosphate as a catalyst in the preparation of heterocyclic compounds from aliphatic amines was early disclosed in U.S. Pat. No. 2,467,205, particularly for the preparation of piperazine from ethylenediamine or from polyethylene polyamine. The use of aluminum phosphate as catalyst in the preparation of triethylenediamine accompanied by piperazine among other by-products is further described in U.S. Pat. No. 3,172,891; while U.S. Pat. No. 3,342,820 describes the use of complex phosphates of alkali metal and trivalent metals in the preparation of C-alkyl TEDA.

U.S. Pat. No. 3,297,701 discloses as catalysts for preparation of TEDA and C-alkyl TEDA, in addition to the preferred aluminum phosphate stated to be superior, other phosphate compounds including calcium and iron phosphates among other listed metal phosphates. In the conversion of N-aminoethylpiperazine to triethylenediamine over aluminum phosphate catalyst, at most up to 39 mol % triethylenediamine is said to be obtained. Other of the named metal phosphate catalysts in the examples of the patent obtain yields of less than 10 mol % TEDA.

Acid metal phosphate catalysts, particularly phosphates of boron, aluminum and trivalent iron, have also been proposed for use in intramolecular cyclic dehydration reactions and other condensation reactions involving amino compounds. Examples of such reactions are found in U.S. Pat. No. 4,117,227, which discloses conversion of an N-substituted diethanolamine to the corresponding N-substituted morpholine. U.S. Pat. No. 4,036,881 describes preparation of non-cyclic polyalkylene polyamines by condensation of an alkylene diamine with an ethanolamine. N-hydroxethylmorpholine is condensed with morpholine in the presence of aluminum phosphate catalyst to form dimorpholino ethane according to U.S. Pat. No. 4,103,087. Similarly, dimorpholinodiethyl ether is obtained by condensation of hydroxyethyl morpholine with aminoethyl morpholine over iron, aluminum or boron phosphate in U.S. Pat. No. 4,095,022. Reaction of piperazine with ethanolamine over such acidic metal phosphate produces N-aminoethyl piperazine according to U.S. Pat. No. 4,049,657.

SUMMARY OF THE INVENTION

It has now been found that unexpectedly high yields of TEDA are selectively obtained when the synthesis thereof is carried out in the presence of catalytic amounts of strontium diorthophosphate —$SrHPO_4$— from a variety of feedstocks including, for example, mono- and di-substituted piperazines, ethanolamines and substituted ethanolamines. It was further found that $SrHPO_4$ can be utilized in other acid catalyzed condensation reactions such as those which heretofore employed catalysts such as silica-alumina, aluminum phosphate or other trivalent metal phosphates.

DETAILED DESCRIPTION OF THE INVENTION

The strontium diorthophosphate is readily prepared by reaction of a dibasic alkali metal phosphate or dibasic ammonium phosphate with a soluble strontium salt at ambient temperatures. High purity and good yields of $SrHPO_4$ are obtained when using the soluble strontium salt of a strong acid, such as strontium nitrate, in substantially stochiometric proportion to the phosphate. In aqueous media under these conditions, the reaction mixture is at a pH of about 5.5.

For use as a catalyst the $SrHPO_4$ product may be employed in the form of irregular particles of desired size range prepared by breaking up the washed and dried filter cake or in the form of regular shaped pellets obtained by known methods of casting, pelletizing or extruding. These catalyst particles may be pure $SrHPO_4$ or diluted or supported by known catalyst substrate materials, such as, for example, alumina, silica, and silica-alumina, and the like.

In using the $SrHPO_4$ to catalyze organic condensation reactions substantially the same conditions may be employed as when using the known catalyst for the particular synthesis. For optimum results, however, some adjustment in operating parameters such as, for example, temperature, diluent, and/or space rate may be found beneficial.

CATALYST PREPARATION

Example 1

200 grams of strontium nitrate [$Sr(NO_3)_2$] was dissolved in distilled water and brought to a total volume of 800 cc with distilled water. To this solution there was added 10 cc of 85% phosphoric acid followed by 34.5 cc of 50% sodium hydroxide added rapidly with vigorous stirring. The resultant fine white precipitate was stirred for 10 minutes, vacuum-filtered and water-washed. The obtained filter cake was air dried in a static oven at approximately 110° C. and broken into small ($\frac{1}{8}$ to $\frac{1}{4}$ inch) irregular pieces for evaluation.

The obtained product had a surface area of 10–15 m$^2$/g. By X-ray diffraction the principal component was identified as $\beta$-SrHPO$_4$ with minor quantities of Sr$_5$(OH)(PO$_4$)$_3$ and unreacted Sr (NO$_3$)$_2$. Infrared spectroscopy showed a spectrum consistent with SrHPO$_4$. (Ref: Richard A. Nygurst and Ronald O. Kagel, "Infrared Spectra of Inorganic Compounds", page 163, 1971).

Example 2

200 grams of Sr(NO$_3$)$_2$ were dissolved in distilled water and diluted to 400 cc. To the obtained solution there was added with vigorous stirring a dibasic ammonium phosphate solution obtained by dissolving 36 grams of (NH$_4$)$_2$HPO$_4$ in distilled water and diluting to 400 cc. The resultant precipitate was filtered, washed with distilled water and dried in air at about 110° C.

By X-ray diffraction and infrared spectroscopy, the obtained product was shown to be essentially pure $\beta$-SrHPO$_4$.

Alpha and beta strontium hydrogen phosphate (strontium diorthophosphate) have substantially different infrared spectra and X-ray diffraction patterns, though the specific detailed crystal structures are not known. Active catalysts may be prepared from either of these crystalline forms. Fresh samples of the product generally show broad infrared bands whereas used samples have sharp infrared spectra and are clearly $\beta$-SrHPO$_4$ regardless of the form of the fresh catalyst.

Example 3

200 grams Sr(NO$_3$)$_2$ was dissolved in distilled water and diluted to 400 cc. To this solution there was added a sodium phosphate solution obtained by diluting 110 grams of 85% H$_3$PO$_4$ with 150 cc distilled water and adding the thus diluted phosphoric acid solution (A) to (B), a solution of 151 grams 50% NaOH diluted with distilled water to 150 cc.

The resultant precipitate was filtered, washed and dried at approximately 110° C. Infrared spectroscopy showed this product to be essentially pure $\beta$-SrHPO$_4$.

Each of the products prepared in accordance with Examples 1 to 3 above were evaluated for catalytic performance by the following test procedure:

A. 20 cc (about 6.2 g) of the catalyst was loaded into a $\frac{3}{4}$" diameter stainless steel tubular reactor.

B. The reactor was placed in a conventional tube furnace such that the catalyst bed was near the furnace center and therefore could be heated to a constant and uniform temperature.

C. The catalyst bed temperature was raised to 320° C. over about 30 minutes while a small flow of gaseous nitrogen was maintained through the reactor.

D. A feed mixture containing hydroxyethylpiperazine (HEP) and water as well as other nitrogen-containing compounds (crude hydroxyethylpiperazine, CHEP) was then allowed to flow through the catalyst bed at a rate of 6.5–7.0 cc/hour; the nitrogen flow was discontinued. Crude hydroxyethylpiperazine typically contains in addition to HEP minor quantities of bis hydroxyethylpiperazine and piperazine.

E. The catalyst bed temperature was raised at a rate of about 10° C./hour to 340°–370° C. Product samples were collected and analyzed. Analyses were performed using well-established gas chromatographic techniques.

The yields obtained are compared in Table 1 below with data from the use of a standard silica-alumina dried gel catalyst employed in the example of U.S. Pat. No. 2,985,658 (designated in Table 1 as Reference Example).

TABLE 1

| CATALYST | EXAMPLE 1* | EXAMPLE 2* | EXAMPLE 3 | REFERENCE EXAMPLE SiO$_2$/Al$_2$O$_3$ |
|---|---|---|---|---|
| Test Temp., °C. | 360 | 360 | 370 | 360 |
| HEP Conversion, Mol % | 99.3 | 99.3 | 95.4 | 100.0 |
| TEDA Yield, Mol % | 83.0 | 93.7 | 82.6 | 39.8 |
| TEDA Selectivity, Mol % | 83.6 | 94.4 | 86.6 | 39.8 |
| Wt. % Recovery | 98.5 | 98.6 | 102.1 | 94.7 |

*Average of two duplicate runs.

Example 4

2000 grams of Sr(NO$_3$)$_2$ were dissolved in 2000 mls of deionized water and the solution diluted to 4000 mls with deionized water after dissolution of the Sr(NO$_3$)$_2$ was complete.

In another container, 1342.3 grams of Na$_2$HPO$_4$ were dissolved in 2000 mls of deionized water. After solution of the Na$_2$HPO$_4$ was complete, the solution was diluted to 4000 mls with deionized water. The pH of this solution was approximately 8.8

Precipitation of SrHPO$_4$ was effected by slowly adding the Na$_2$HPO$_4$ solution to the Sr(NO$_3$)$_2$ solution with rapid stirring. The white SrHPO$_4$ precipitated rapidly from solution forming a rather thick slurry. This slurry was mixed for one hour, after which time the pH was measured to be about six.

The solid SrHPO$_4$ was recovered by filtering on an eight frame filter press using cloth filters. It was washed with deionized water. After filtering and washing, the solid was dried in a circulating hot air oven at 250° F. for four hours. The yield of SrHPO$_4$ was 1680 grams. The solid was wetted and formed into pellets by extrusion through a 3.1 mm die plate and cutting the extrudates to about $\frac{1}{4}$ inch in length. After drying the extrudate at 250° F. for four hours in a circulating hot air oven, they were heat treated at 662° F. for two hours in a 20% steam, 80% air atmosphere.

Example 5

The catalyst of Example 4 was tested in the conversion of crude HEP to TEDA. The reaction was carried out at atmospheric pressure, at a liquid hourly space velocity of 0.3 and at the temperatures indicated in Table 2 below.

TABLE 2

|  | Initial | After 78 Days |
|---|---|---|
| Bed Temp., °C. | 360 | 368 |
| HEP Conversion, wt. % | 99+ | 99+ |
| TEDA Yield, wt. % | 40.5 | 43.0 |
| Piperazine Yield, wt. % | 13.5 | 18.5 |

Example 6

The catalyst of Example 4 was tested for the conversion of diethanolamine to TEDA. The test was carried out at 370° C. using a feed consisting of diethanolamine and water (2.0:1.0 mole ratio) pumped into the reactor at a rate of 4.4 liquid cc/hr along with helium diluent at a rate of 25 cc/minute. The diethanolamine was completely converted to TEDA as the only recovered product.

Example 7

A 64% by weight solution of N-aminoethyl piperazine in water was passed over a catalyst composition consisting essentially of SrHPO$_4$ at 380° C. and at a liquid hourly space velocity of 0.3 volumes of liquid per volume of catalyst. In a first pass operation there was obtained 96.8% conversion of the feed compound, obtaining a yield of 34.8% by weight (40.1 mol %) TEDA and 27.1% by weight (40.6 mol %) piperazine.

Example 8

Morpholine was reacted with dimethylethanolamine in substantially stoichiometric proportions in the presence of water over SrHPO$_4$ catalyst at a temperature of 360° C. and at a LHSV of 0.3. The organic reaction product contained 27% of dimethylaminoethylmorpholine; which has the structural formula:

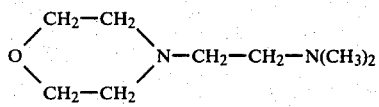

Other typical condensation reactions in which SrHPO$_4$ may be employed as a catalyst include the formation of amines by amination of the corresponding alcohols with ammonia and the formation of polyamines from glycols and diamines.

It is believed that the key to the properties of the SrHPO$_4$ as a highly selective catalyst is due to the presence of a specific structure, which provides a narrow range of acidity. This narrow acidity range displayed by SrHPO$_4$ may be optimum for promoting certain types of acid catalyzed reactions, in contrast to such catalysts as alumina, silica-alumina and the like which have acid sites of widely varying strength, and hence show relatively low selectivity for the desired reaction.

Example 9

Diethyleneglycol was passed over SrHPO$_4$ catalyst in the presence of water at a temperature of 370° and at a contact time of 6.7 seconds. The feed contained 57 vol % diethylene glycol and 43 vol % H$_2$O. The reaction product contained 33 wt. % 1,4-dioxane, corresponding to a yield of 47 mol %.

The addition of water to the organic feeds may be desirable to prevent loss of catalyst activity as a result of dehydration of the SrHPO$_4$ to the pyrophosphate.

Example 10

The SrHPO$_4$ catalyst of Example 4 was tested for the conversion of 1, 4-butanediol to tetrahydrofuran. The test was carried out at 350° C. using a feed consisting of 20 percent by volume of water and 80 percent by volume of 1, 4-butanediol pumped to the tubular reactor at a rate of 4.4 cc/hr. Helium diluent was also fed at the rate of 30 cc/min. Under these conditions, the diol was completely converted to tetrahydrofuran.

What is claimed is:

1. In a method for synthesis of triethylenediamine from nitrogen-containing compounds selected from the group consisting of hydroxyethylpiperazine, crude hydroxyethylpiperazine, N-aminoethyl piperazine, ethanolamines and substituted ethanolamines by condensation reactions in the presence of acidic catalyst, the improvement which comprises the use as such catalyst of a product consisting essentially of SrHPO$_4$.

2. The method as defined in claim 1 wherein said SrHPO$_4$ is associated with a carrier from the group consisting of silica, alumina and silica-alumina.

3. The method as defined in claim 1 wherein such condensation reaction is one resulting in the elimination of water.

4. The method as defined in claim 1 wherein such condensation reaction is one resulting in the elimination of ammonia.

5. The method as defined in claim 1 wherein such condensation reaction comprises the production of triethylenediamine from hydroxyethylpiperazine.

6. The method as defined in claim 1 wherein such condensation reaction comprises the production of triethylenediamine from crude hydroxyethylpiperazine.

7. The method as defined in claim 1 wherein such reaction comprises the production of triethylene diamine from ethanolamines.

8. The method as defined in claim 1 wherein such condensation reaction comprises the production of triethylenediamine from N-aminoethyl piperazine.

9. The method as defined in any one of claims 5, 6 or 8, wherein the reaction is carried out in the presence of water.

* * * * *